United States Patent [19]

White

[11] 4,380,652

[45] Apr. 19, 1983

[54] ENAMINES OF 6′-METHYLSPECTINOMYCIN AND PROCESS FOR PREPARING THE SAME

[75] Inventor: David R. White, Kalamazoo, Mich.

[73] Assignee: The Upjohn Company, Kalamazoo, Mich.

[21] Appl. No.: 285,165

[22] Filed: Jul. 20, 1981

[51] Int. Cl.³ .................. C07D 319/20; C07D 327/06
[52] U.S. Cl. ........................................ 549/361; 549/16
[58] Field of Search ................ 549/16, 361; 260/340.3

[56] References Cited

U.S. PATENT DOCUMENTS 3,981,887  9/1976  Gante et al. .......................... 549/16
4,282,152  8/1981  White ................................ 260/340.3

FOREIGN PATENT DOCUMENTS 734469  5/1966  Canada .

Primary Examiner—Ethel G. Love
Attorney, Agent, or Firm—Sidney B. Williams, Jr.

[57] ABSTRACT

A method for the preparation of 6′-methylspectinomycin and analogs thereof. Additionally provides novel intermediates utilized in said method.

6 Claims, No Drawings

ENAMINES OF 6'-METHYLSPECTINOMYCIN AND PROCESS FOR PREPARING THE SAME

FIELD OF THE INVENTION

The invention concerns a method for the synthesis of 6'-methyl spectinomycin and analogs thereof including intermediates utilized in the method.

DESCRIPTION OF THE PRIOR ART

Spectinomycin A is a known antibiotic and was first prepared by a microbiological process. See Bergy et al., U.S. Pat. No. 3,234,092.

Some analogs of spectinomycin are described by Rosenbrook Jr. et al., in J. Antibiotics, 28, pp. 953 and 960 (1975) and J. Antibiotics, 31, p. 451 (1978). In addition, Carney et al. describe chlorodeoxy derivatives of spectinomycin in J. Antibiotics, 30, 960 (1977). Further, 9-epi-4(R)-dihydrospectinomycin is reported by Foley et al., in J. Org. Chem., 43, 22 pp. 4355–4359 (2978). However, biological activity is not reported for any of the spectinomycin analogs and derivatives disclosed in the above-cited references.

Lemieux, Can. J. Chem., 51, p. 53 (2973) teaches a preferential reaction at the 5-hydroxyl of 2-deoxystreptamine (1) with tri-O-acetyl-2-deoxy-2-nitroso-α-D-glycopyranosyl chloride (2) to give a α-pseudodisaccharide wherein CBz is carbobenzyloxy. Mallams et al., J. Chem. Soc. Perkin I, p. 1118 (2976), extend the Lemieux reaction to synthesize di- and tri-saccharides.

Removal of oximes is taught by Lemieux et al., Can. J. Chem. 51, p. 19 (1973) and Mallams et al., J. Chem. Soc. Perkin I, p. 1097 (1976).

Hannessian et al., (1979), describe a chemical synthesis of spectinomycin.

White et al., Tetrahedron Letters, July, 1979, disclose a chemical synthesis of spectinomycin and analogs thereof. The same synthesis is disclosed in Ser. No. 150,530, filed May 26, 1980, now U.S. Pat. No. 4,351,771, which is a continuation of Ser. No. 020,172, filed Mar. 3, 1979, now abandoned.

SUMMARY OF THE INVENTION

An enoneacylate is converted to 6'-methylspectinomycin and analogs thereof. The sequence employs several versatile intermediates. The invention involves modification of C-6' using an enoneacylate.

DETAILED DESCRIPTION OF THE INVENTION

More specifically, this invention relates to a process for preparing compounds of Formula I which involves utilizing an enoneacylate VI as the starting material. The formulae referred to are set forth in Chart A. The process can be represented and illustrated in the reaction sequence of Scheme I, wherein R is hydrogen or lower alkyl, $R_1$ through $R_9$ are selected from the group consisting of hydrogen, lower alkyl, lower alkenyl, and lower alkynyl; $R'_2$, $R'_3$, $R'_6$ and $R'_7$ are selected from the group consisting of lower alkyl, lower alkenyl, lower alkynyl, and a blocking group selected from the group consisting of aralkoxycarbonyl, halogenated alkoxycarbonyl and alkoxycarbonyl; with the proviso that one of $R_2$ and $R_3$ is always hydrogen and one of $R_6$ and $R_7$ is always hydrogen, and the further proviso that one of $R'_2$ and $R'_3$ is always a blocking group and one of $R'_6$ and $R'_7$ is always a blocking group; $R_{10}$ is acyl. A is selected from the group consisting of oxygen and sulfur, and B and $B_1$ are the same or different and are selected from the group consisting of hydrogen, hydroxy, alkoxy, o-lower alkenyl, thio, thio-lower alkyl and thio-lower alkenyl. Some of the intermediates and processes between VI and II are disclosed in Ser. No. 020,073, filed Mar. 13, 1979.

The numbering of carbons shown in compound I will be used in discussions thereof throughout the specification.

The compounds prepared by the process of this invention include the hydrate forms of compounds of Formula I. These compounds are hydrated at the 3' position and have the Formula I';

wherein A, B, $B_1$, and $R_1$ through $R_{10}$ are the same as defined above. Also included are pharmaceutically acceptable salts of the compounds of formulae I and I'.

"Lower alkyl" means methyl, ethyl, propyl, butyl, pentyl, hexyl, heptyl, octyl, and the isomeric forms thereof.

"Lower alkenyl" means ethenyl, propenyl, butenyl, pentenyl, hexenyl, heptenyl, octenyl and the isomeric forms thereof.

"Lower alkynyl" means ethylyl, propynyl, butynyl, pentynyl, hexynyl, heptynyl, octynyl and the isomeric forms thereof.

"Acyl" means formyl, acetyl, propionyl, butylyl and pentinoyl.

"Halogenated alkoxycarbonyl" means mono-, di-, tri-halomethoxycarbonyl; mono-, di-, tri-haloethoxycarbonyl; mono-, tri-halopropoxycarbonyl; mono-, di-, tri-halobutoxycarbonyl, mono-, di-, tri-halopentoxycarbonyl and isomeric forms thereof.

"Halo" means fluoro, chloro, bromo and iodo.

"Aralkoxycarbonyl" means benzyloxycarbonyl, phenethoxycarbonyl, phenpropoxycarbonyl, diphenyloctoxycarbonyl and isomeric forms thereof and fluoroenylmethoxy carbonyl.

"Alkoxycarbonyl" means isopropyloxy carbonyl, tertiary-butyloxy carbonyl, and tertiary-pentyloxycarbonyl.

It is meant that as used in this description and in the appended claims that when more than one hydroxy or alkoxy is present on the sugar moiety herein they may be the same or different.

The invention also includes novel intermediates II', III and V. The dienone III is a highly versatile Michael acceptor; an excellent intermediate for modification. In Formula II', $R_{11}$ is lower alkyl.

Thus, the invention process realizes the importance of the stereochemistry at the glycosidic bond, i.e., 1' position of compounds of Formula I.

The term "α-anomer" means a 1' substituent below the plane of the ring system and the term "β-anomer" means that anomers having the C-1' configuration corresponding to spectinomycin.

Compounds prepared by the process of this invention which exhibit desirable biological activity are β-anomers of compound I. This glycosidic configuration is found in spectinomycin shown in Chart A and are designated by the script a. Therefore, adequate selectivity at the 1' position is desirable to obtain biologically active analogs of spectinomycin.

In Step 1, enoneacylate VI is reacted with dimethylformamide dimethyl acetal in a solvent to yield the enamine V. The temperature range of the reaction is generally 25° C. to reflux, preferably 40° C. to 80°. Time of the reaction may range from 1 hr. to 48 hrs., preferably 2 hrs. to 10 hrs. Dimethylformamide dimethylacetal is used in excess. The preferred reaction time and solvent are 7 hrs. and dimethylformamide. Other acetals of dimethylformamide such as di-t-butyl can also be used.

The starting enoneacetate and methods for preparing it are described in U.S. application Ser. No. 150,530 filed May 16, 1980.

The enamine can be isolated from the mixture by conventional procedures such as extraction, chromatography and combinations thereof.

In Step 2 side chain reduction of the enamine V is effectuated under standard cyanoborohydride conditions to yield amine IV. The amine can be isolated from the reaction mixture by conventional means such as extraction, chromatography and combinations thereof.

Step 3 involves reacting amine IV with an alkyl halide in the presence of a solvent to yield dienone III. The reaction can be conducted at a temperature of about 0° to about 100°, for a time period of about 1 hr. to about 30 hrs., and using an excess of methyl iodide. The preferred reaction temperature and times are 20° C. to 40° C., 1 hr. to 20 hrs. Solvents that can be used include methylene chloride, $CHCl_3$, THF, and ether. The preferred solvent is methylene chloride.

In Step 4, dienone III is subjected to reduction to yield the blocked 6'-methylspectinomycin. This is a very critical step in the process for several reasons. It is very difficult to reduce the 4',5' double bond without reducing the 3' carbonyl. Palladium catalysts, i.e. 10% palladium on barium sulfate (ionic palladium, brown catalyst), can be used with partial success, as described above, but the blocking groups, especially carbobenzyloxy groups, are removed so the separation problem is made more difficult. Furthermore, palladium catalysts do not work on analogs with more highly substituted sugar side chains. Therefore, platinum oxide in the presence of a solvent and a base is preferred.

A second major advantage is that the protecting groups remain so that products can be purified by chromatography before using one of several deprotecting methods. The reaction is conducted by dissolving dienone III in the solvent, adding the base, platinum oxide and then contacting the mixture with hydrogen. The reduction is conducted at a temperature of from about 20° to 40°, for a period of about 1 hr. to 4 hrs. Preferred temperature and reaction times are 20° C. and 300° C. and 2 hrs. to 3 hrs., respectively.

In Step 5 the compound of Formula II is deprotected to yield the compound of Formula I. The particular conditions of deprotection depends upon the particular groups, i.e. group $R'_2$ or $R'_3$ and $R'_6$ or $R'_7$ that block the amine on the actinamine ring. Where that group is benzyloxy carbonyl or aralkoxy carbonyl the deprotection can be conducted under from $-10$ psi to $+200$ psi of hydrogen over a conventional catalyst such as palladium black, palladium on carbon, palladium on barium sulfate, or palladium on barium carbonate, while suspended in a solvent, for example, isopropanol, absolute ethanol, ethyl acetate, toluene or tetrahydrofuran.

Alternatively, deblocking of compounds wherein $R'_2$ $R'_3$ and $R'_6$ or $R'_7$ are alkoxycarbonyl or aryloxycarbonyl can be conducted in the presence of an acid in solvent such as nitromethane and methylene chloride.

When $R'_2$ or $R'_3$ and $R'_6$ or $R'_7$ are haloalkoxycarbonyl, the deblocking is preferably conducted in the presence of zinc.

Any method within the skill in the art may be used for isolation of an analog or asteric mixture of a compound having Formula I and methods disclosed herein are not meant to be limiting. If isolation is conducted under anhydrous conditions, compounds having a carbonyl group at the 3' position (Formula I) are obtained. If conducted under aqueous conditions, compounds hydrated at the 3' position (Formula I') are obtained. One such method includes evaporation of the excess solvent and formation of a crystalline salt of the compound. These salts may be formed using a solution of an acid such as toluene sulfonic acid, hydrochloric acid, hydrobromic acid, hydroiodic acid or other acids in a solvent such as water, methanol, ethanol, isopropanol, ether, 1,2-dimethoxyethane or p-dioxane. The salt is isolated by filtration and direct crystallization or by evaporation of the solvent followed by subsequent recrystallization from a suitable solvent.

Alternatively, the crude analogs may be purified by adsorption on a column of a weakly acidic ion exchange resin such as Amberlite IRC-50 or CG-50 followed by elution with a solvent such as water, methanol, ethanol, ether, tetrahydrofuran, 1,2-dimethoxy, 1,2-dimethoxy ethane or p-dioxane containing hydrochloric acid, hydrobromic acid, hydroiodic acid and sulfuric acid.

Each step of the above process can be conducted on asteric mixtures of various anomers or on the desired $\beta$ anomer itself obtained by resolution or separation at any stage in the process. The remaining steps may be conducted on $\beta$-intermediates resulting in the desired biologically active isomers.

Acid salts can be made by neutralizing compounds of Formula I with the appropriate acid to below about pH 7.0 and advantageously to about pH 2 to pH 3. Suitable acids for this purpose include hydrochloric, sulfuric, phosphoric, sulfamic, hydrobromic. and the like. Acid and base salts of the compounds can be used for the same biological purposes as the parent compound.

The compounds of Formula I inhibit the growth of microorganisms in various environments. For example, Formula I conpounds having the $\beta$ configuration are active against *Escherichia coli* and can be used to reduce, arrest, and eradicate slime production in papermill systems caused by its antibacterial action against this microorganism. These $\beta$ anomers also can be used to prolong the life of cultures of *Trichomonas foetus, Trichomonas hominis,* and *Trichomonas vaginalis* by freeing them of *Escherichia coli* contamination. Still further, $\beta$ anomers are active against *Bacillus subtilis* so it can be used to minimize or prevent odor in fish or fish crates caused by this organism. Also, the anomers can be used to swab laboratory benches and equipment in a mycological laboratory. $\beta$-anomers are also effective against *Klebsiella pneumoniae.*

The compounds of Formula I are also effective for treating bacterial infections, such as gonorrhea in mammals, including humans.

The compositions of the present invention are presented for administration to humans and animals in unit dosage forms, such as sterile parenteral solutions or suspensions, eye drops and water-in-oil emulsions containing suitable quantities of the compound of Formula I.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspension can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term "unit dosage form" as used in the specification refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are ampoules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans of from about 2 to about 4000 mg of compound in a single dose, administered parenterally or in the compositions of this invention, are effective for bacterial infections. More specifically, the single dose is from 5 mg to about 200 mg of compound.

The following described preparations of analogs of spectinomycin and intermediates useful in the preparation thereof are indicative of the scope of this invention and are not to be construed as limitative. Those skilled in the art will promptly recognize variations from the procedures both in the analogs and analog precursors within the novel compounds described as well as reaction conditions and techniques of the invention process.

For example, for each of the Preparations and Examples in the following descriptions, corresponding stereoisomers for each named compound is contemplated to be within the scope of the invention.

PREPARATION 1

N,N-dicarbobenzyloxy-2'-O-acetyl-6-[(dimethylamino)methylene]-4',5'-didehydrospectinomycin A solution of N,N'-dicarbobenzyloxy-2'-O-acetyl-4',5'-didehydrospectinomycin (22.00 g, 34.4 mmole) and dimethylformamide dimethylacetal (100 ml) in dimethylformamide (100 ml) is stirred for 7 hours at 50°–55° C. with drierite protection. The brown solution is concentrated under vacuum and the residue chromatographed on silica gel (250 g) which has been wet packed in a 2 liter sintered glass funnel. The mixture is eluted with 5% acetonitrile in chloroform (2 liters), 7% (3 liters), 33% (3 liters), 50% (6 liters) over a period of 1½ hours. Half liter fractions are taken. The fractions are evaluated by TLC (1/1 acetonitrile in chloroform) and combined to give 19.78 g of pure N,N-dicarbobenzyloxy-2'-O-acetyl-6-[(dimethyl-amino)methylene]-4',5'-didehydrospectinomycin and 3.30 g of N,N-dicarbobenzyloxy-2'-O-acetyl-6-[(dimethyl-amino)-methylene]-4',5'-didehydrospectinomycin containing some DMF (dimethyl formamide). The latter fraction was rechromatographed as above (but using 60 g of silica gel) to give 2.75 g of pure N,N-dicarbobenzyloxy-2'-O-acetyl-6-[(dimethylamino)-methylene]-4',5'-didehydrospectinomycin. Total yield is 22.53 g (94% yield).

$CD(CH_3OH)[\theta]_{311}nm$—$10,400 \pm 1,200$, $[\theta]_{285}$—$2,500 \pm 1,200$, $[\theta]_{246}$—$1,200 \pm 1,200$.

IR(mull): 3380, 1750, 1695, 1675sh, 1600, 1555, 1500, 1385, 1350, 1280, 1240, 1195, 1185, 1145, 1110, 1085, 1065, 1025, 1000, 960, 770, 740, 645 $cm^{-1}$.

PMR ($CDCl_3$): 2.13 (3H, s), 2.82 (3H, s), 2.89 (6H, br.s), 2.91 (3H, s), 5.10 (4H, br.s), 5.16 (1H, s), 5.97 (1H, s), 7.30δ (10H, s).

CMR ($CD_3COCD_3$): 20.9, 31.2, 31.5, 30–44 br, 36.3, 59.6, 66.2, 67.3, 74.6, 75.4, 88.7, 94.9, 95.0, 95.1, 95.5, 128.3, 129.1, 137.9, 138.0, 150.3, 157.2, 157.7, 163.3, 169.8, 171.2, 180.3 PPM.

Mass spectrum, m/c (diTMS): 839 (M+), 824, 797, 779, 730, 688. Peak matched calcd: 839.3480; Found: 839.3466.

Utilizing a procedure similar to Preparation 1, but substituting the appropriately-substituted enone acetate for N,N'-dicarbobenzyloxy-2'-O-acetyl-4',5'-didehydrospectinomycin, there are obtained the enamines of Tables I and II.

TABLE I

| B | $B_1$ | $R_{10}$ |
|---|---|---|
| HO— | HO— | $CH_3\overset{O}{\underset{\|}{C}}-$ |
| $CH_3O-$ | HO— | $CH_3\overset{O}{\underset{\|}{C}}-$ |
| $C_2H_5O-$ | HO— | $CH_3\overset{O}{\underset{\|}{C}}-$ |
| HS— | HO— | $CH_3\overset{O}{\underset{\|}{C}}-$ |
| $CH_3S-$ | HO— | $CH_3\overset{O}{\underset{\|}{C}}-$ |
| $C_2H_5S-$ | HO— | $CH_3\overset{O}{\underset{\|}{C}}-$ |

TABLE I-continued

[Structure: cyclohexane ring with CBz-N(CH₃) and H₃C-N(CBz) substituents, B and B₁ groups, connected via ketone-O-CH to side chain with OR₁₀, ketone, and vinyl-N(CH₃)₂]

| B | B₁ | R₁₀ |
|---|----|-----|
| H— | HO— | CH₃C(=O)— |
| HO— | H— | CH₃C(=O)— |
| HO— | CH₃O— | CH₃C(=O)— |
| HO— | C₂H₅O— | CH₃C(=O)— |
| HO— | HS— | CH₃C(=O)— |
| HO— | CH₃S— | CH₃C(=O)— |
| HO— | C₂H₅S— | CH₃CH₂C(=O)— |
| HO— | HO— | CH₃(CH₂)₂C(=O)— |
| HO— | HO— | CH₃(CH₂)₂C(=O)— |
| HO— | HO— | CH₃(CH₂)₂C(=O)— |
| HO— | HO— | CH₃(CH₂)₂C(=O)— |
| HO— | HO— | CH₃(CH₂)₃C(=O)— |
| HO— | HO— | isopropionyl |
| HO— | HO— | sec-butyryl |
| HO— | HO— | t-butyryl |

TABLE II

[Structure: cyclohexane ring with CBz-N(CH₃) and H₃C-N(CBz) substituents, B and B₁ groups, with S configuration, connected via ketone-O-CH to side chain with OR₁₀, ketone, and vinyl-N(CH₃)₂]

| B | B₁ | R₁₀ |
|---|----|-----|
| HO— | HO— | CH₃C(=O)— |
| CH₃O— | HO— | CH₃C(=O)— |
| C₂H₅O— | HO— | CH₃C(=O)— |
| HS— | HO— | CH₃C(=O)— |
| CH₃S— | HO— | CH₃C(=O)— |
| C₂H₅S— | HO— | CH₃C(=O)— |
| H— | HO— | CH₃C(=O)— |
| HO— | H— | CH₃C(=O)— |
| HO— | CH₃O— | CH₃C(=O)— |
| HO— | C₂H₅O— | CH₃C(=O)— |
| HO— | H₂— | CH₃C(=O)— |
| HO— | CH₃S— | CH₃C(=O)— |
| HO— | C₂H₅S— | CH₂CH₂C(=O)— |
| HO— | HO— | CH₂CH₂C(=O)— |
| HO— | HO— | CH₃(CH₂)₂C(=O)— |
| HO— | HO— | CH₃(CH₂)₂C(=O)— |
| HO— | HO— | CH₃(CH₂)₃C(=O)— |
| HO— | HO— | CH₃(CH₂)₃—C(=O)— |
| HO— | HO— | isopropionyl |
| HO— | HO— | sec-butyryl |

TABLE II-continued

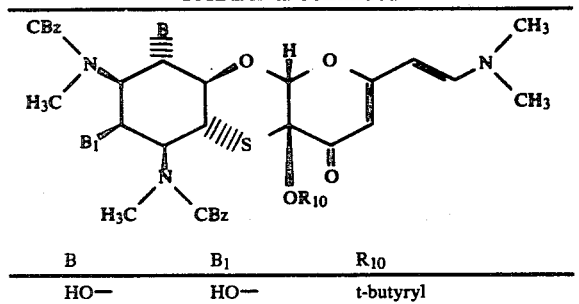

| B | B₁ | R₁₀ |
|---|---|---|
| HO— | HO— | t-butyryl |

PREPARATION 2

N,N'-dicarbobenzyloxy-2-O'-acetyl-6'-(dimethylaminomethyl)-4',5'-didehydrospectinomycin N,N-dicarbobenzyloxy-2'-O-acety-6'-[(dimethylamino)methylene]4', 5'-didehydrospectinomycin (20.00 g, 28.78 mmole) and methyl orange (5 mg) are dissolved in methanol (200 ml). The pH is adjusted to 4 with 2 N methanolic hydrogen chloride and sodium cyanoborohydride is added in portions over 20 minutes with frequent readjustment to pH using 2 N methanolic hydrogen chloride. After a total of 2.00 g (31.83 mmole) of sodium cyanoborohydride has been added, the solution is stirred an additional hour at room temperature; TLC (1:9 methanol/chloroform) shows starting material has been consumed. The solution is concentrated, diluted with ethyl acetate (500 ml), 0.1 N sodium hydroxide (250 ml), 1.0 N NaOH (25 ml) and saturated brine (250 ml). The organic phase is washed with brine (200 ml). The three aqueous phases are washed in sequence with ethyl acetate (2×200 ml). Organic extracts are dried over sodium sulfate and concentrated to yield N,N'-dicarbo-benzyloxy-2-O'-acetyl-6'-dimethylaminomethyl)-4', 5'-dideydrospectinomycin as a foam (17.93 g, 89% yield).

CD(CH₃OH): $[\theta]_{321}$—12,000±1,100, $[\theta]_{270}$±1,100.
UV (C₂H₅OH): 273 nm (8,800), 377 nm(sh) (63).
PMR (CDCl₃): 2.13 (3H, s), 2.17 (6H, s), 2.46 (3H, s), 3.05 (3H, s), 3.06 (3H, s), 5.05 (4H, d), 5.34 (1H, s), 5.89 (1H, s), 7.26 (10H, d).
CMR (CD₃COCD₃): 20.9, 31.3, 45., 56.1, 57.1, 61.3, 66.1, 67.3, 74.0, 75.4, 93.7, 96.0, 103.1, 128.3, 129.1, 137.9, 157.2, 170.0, 174.9, 183.1 ppm.

Using a procedure similar to that of Preparation 2 but substituting the appropriately substituted precursor enamines from Tables I and II for the N,N'-dicarbobenzyloxy-2'-O-acetyl-6'-[(dimethylamino)methylene]-4',5'-didehydrospectinomycin, there is obtained the protected spectinomycin analogs of Tables III and IV.

TABLE III

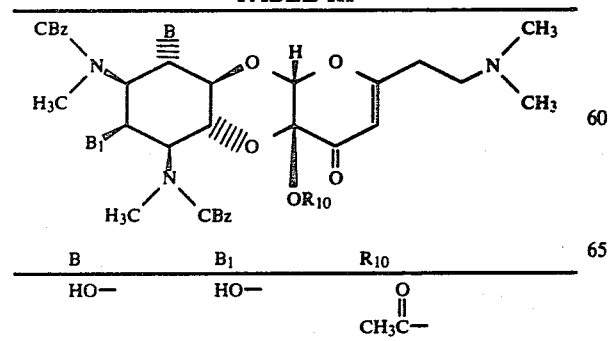

| B | B₁ | R₁₀ |
|---|---|---|
| HO— | HO— | O‖CH₃C— |

TABLE III-continued

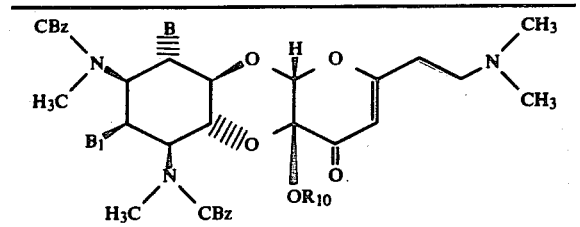

| B | B₁ | R₁₀ |
|---|---|---|
| CH₃O— | HO— | O‖CH₃C— |
| C₂H₅O— | HO— | O‖CH₃C— |
| HS— | HO— | O‖CH₃C— |
| CH₃S— | HO— | O‖CH₃C— |
| C₂H₅S— | HO— | O‖CH₃C— |
| H— | HO— | O‖CH₃C— |
| HO— | H— | O‖CH₃C— |
| HO— | CH₃O— | O‖CH₃C— |
| HO— | C₂H₅O— | O‖CH₃C— |
| HO— | HS— | O‖CH₃C— |
| HO— | CH₃S— | O‖CH₃C— |
| HO— | C₂H₅S— | O‖CH₃CH₂C— |
| HO— | HO— | O‖CH₂CH₂C— |
| HO— | HO— | O‖CH₃(CH₂)₂C— |
| HO— | HO— | O‖CH₃(CH₂)₂C— |
| HO— | HO— | O‖CH₃(CH₂)₂C— |
| HO— | HO— | O‖CH₃(CH₂)₃—C— |
| HO— | HO— | isopropionyl |
| HO— | HO— | sec-butyryl |

TABLE III-continued

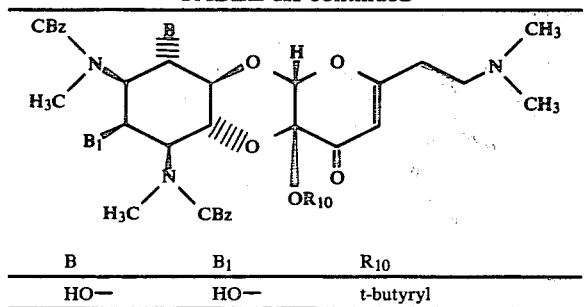

| B | B₁ | R₁₀ |
|---|---|---|
| HO— | HO— | t-butyryl |

TABLE IV

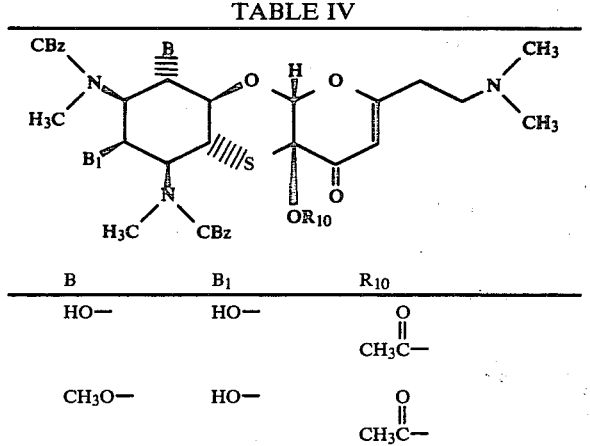

| B | B₁ | R₁₀ |
|---|---|---|
| HO— | HO— | CH₃C(O)— |
| CH₃O— | HO— | CH₃C(O)— |
| C₂H₅O— | HO— | CH₃C(O)— |
| HS— | HO— | CH₃C(O)— |
| CH₃S— | HO— | CH₃C(O)— |
| C₂H₅S— | HO— | CH₃C(O)— |
| H— | HO— | CH₃C(O)— |
| HO— | H— | CH₃C(O)— |
| HO— | CH₃O— | CH₃C(O)— |
| HO— | C₂H₅O— | CH₃C(O)— |
| HO— | HS— | CH₃C(O)— |
| HO— | CH₃S— | CH₃C(O)— |
| HO— | C₂H₅S— | CH₃CH₂C(O)— |

TABLE IV-continued

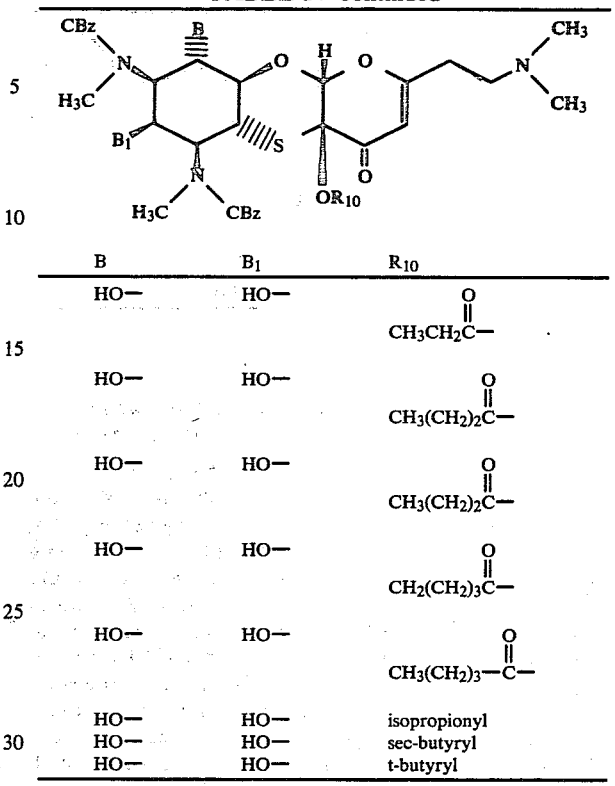

| B | B₁ | R₁₀ |
|---|---|---|
| HO— | HO— | CH₃CH₂C(O)— |
| HO— | HO— | CH₃(CH₂)₂C(O)— |
| HO— | HO— | CH₃(CH₂)₂C(O)— |
| HO— | HO— | CH₂(CH₂)₃C(O)— |
| HO— | HO— | CH₃(CH₂)₃—C(O)— |
| HO— | HO— | isopropionyl |
| HO— | HO— | sec-butyryl |
| HO— | HO— | t-butyryl |

PREPARATION 3

N,N'-dicarbobenzyloxy-2-O'-acetyl-6'-methylene-4',5'-didehydrospectinomycin

N,N'-dicarbobenzyloxy-2-O'-acetyl-6'-(dimethylaminomethyl)-4',5'-didehydrospectinomycin (17.43 g, 25.00 mmole) is dissolved in methylene chloride (200 ml) and methyl iodide (18.0 ml, 41.04 g, 289 mmole) and stirred at room temperature for 6 hours. After standing at 10° C. for an additional 16 hours the solution is concentrated and then dissolved in 1/9 acetonitrile/chloroform. The mixture is chromatographed on silica gel (300 g) using the same solvent (4 liters), then ⅓ acetonitrile/chloroform (4 liters). The first pure substance eluted is obtained by combining fractions and concentrate to yield 10.03 g of N,N'-dicarbobenzyloxy-2-O'-acetyl-6'-methylene-4',5'-didehydrospectinomycin (61% yield).

CD (CH₃OH): $[\theta]_{334}$—26,100±2,300, $[\theta]_{240}$—44,800±2,300, $[\theta]_{244}$ nm—10,800±2.300.

UV (C₂H₅OH): 204sh (22.500), 241 (6,750) 250sh (5,900), 256sh (4,900), 293 nm (14,650).

PMR (CDCl₃): 2.13 (3H, s), 3.03 (3H, s), 3.06 (3H, s), 5.05 (4H, d), 5.44 (1H, s), 5.61 (1H, q), 5.95 (1H, s), 6.11 (1H, s), 6.19 (1H, s), 7.29 pp (10H, s).

CMR (CD₃COCD₃): 20.9, 31.4, 57.2, 60.1, 66.2, 67.4, 74.1, 74.7, 75.6, 94.0, 96.1, 104.3, 125.3, 128.4, 129.2, 131.1, 138.0, 138.1, 157.6, 166.6, 170.2, 184.0 ppm.

Using a procedure similar to that of Preparation 3 but substituting the appropriately substituted didehydrospectinomycin for N,N'-dicarbobenzyloxy-2-O'-acetyl-6'-(dimethylaminomethyl)-4',5'-didehydrospectinomycin, there is obtained the protected spectinomycin analogs of Tables V and VI.

TABLE V

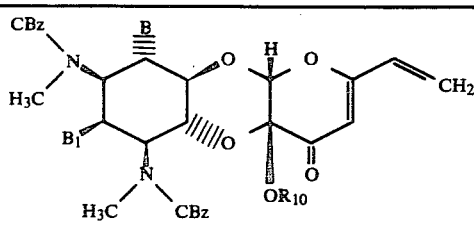

| B | B₁ | R₁₀ |
|---|---|---|
| HO— | HO— | $CH_3\overset{O}{\underset{\|}{C}}-$ |
| $CH_3O-$ | HO— | $CH_3\overset{O}{\underset{\|}{C}}-$ |
| $C_2H_5O-$ | HO— | $CH_3\overset{O}{\underset{\|}{C}}-$ |
| HS— | HO— | $CH_3\overset{O}{\underset{\|}{C}}-$ |
| $CH_3S-$ | HO— | $CH_3\overset{O}{\underset{\|}{C}}-$ |
| $C_2H_5S-$ | HO— | $CH_3\overset{O}{\underset{\|}{C}}-$ |
| H— | HO— | $CH_3\overset{O}{\underset{\|}{C}}-$ |
| HO— | H— | $CH_3\overset{O}{\underset{\|}{C}}-$ |
| HO— | $CH_3O-$ | $CH_3\overset{O}{\underset{\|}{C}}-$ |
| HO— | $C_2H_5O-$ | $CH_3\overset{O}{\underset{\|}{C}}-$ |
| HO— | $H_2$ | $CH_3\overset{O}{\underset{\|}{C}}-$ |
| HO— | $CH_2S-$ | $CH_3\overset{O}{\underset{\|}{C}}-$ |
| HO— | $C_2H_5S-$ | $CH_2CH_2\overset{O}{\underset{\|}{C}}-$ |
| HO— | HO— | $CH_2CH_2\overset{O}{\underset{\|}{C}}-$ |
| HO— | HO— | $CH_2(CH_2)_2\overset{O}{\underset{\|}{C}}-$ |
| HO— | HO— | $CH_3(CH_2)_2\overset{O}{\underset{\|}{C}}-$ |
| HO— | HO— | $CH_3(CH_2)_3\overset{O}{\underset{\|}{C}}-$ |
| HO— | HO— | $CH_3(CH_2)_3-\overset{O}{\underset{\|}{C}}-$ |

TABLE V-continued

| B | B₁ | R₁₀ |
|---|---|---|
| HO— | HO— | isopropionyl |
| HO— | HO— | sec-butyryl |
| HO— | HO— | t-butyryl |

TABLE VI

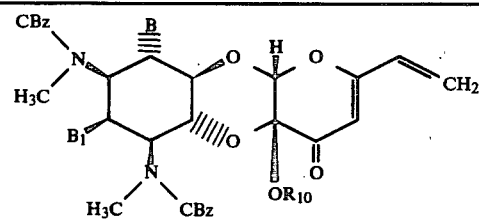

| B | B₁ | R₁₀ |
|---|---|---|
| HO— | HO— | $CH_3\overset{O}{\underset{\|}{C}}-$ |
| $CH_3O-$ | HO— | $CH_3\overset{O}{\underset{\|}{C}}-$ |
| $C_2H_5O-$ | HO— | $CH_3\overset{O}{\underset{\|}{C}}-$ |
| HS— | HO— | $CH_3\overset{O}{\underset{\|}{C}}-$ |
| $CH_3S-$ | HO— | $CH_3\overset{O}{\underset{\|}{C}}-$ |
| $C_2H_5S-$ | HO— | $CH_3\overset{O}{\underset{\|}{C}}-$ |
| H— | HO— | $CH_3\overset{O}{\underset{\|}{C}}-$ |
| HO— | H— | $CH_3\overset{O}{\underset{\|}{C}}-$ |
| HO— | $CH_3O-$ | $CH_3\overset{O}{\underset{\|}{C}}-$ |
| HO— | $C_2H_5O-$ | $CH_3\overset{O}{\underset{\|}{C}}-$ |
| HO— | HS— | $CH_3\overset{O}{\underset{\|}{C}}-$ |
| HO— | $CH_3S-$ | $CH_3\overset{O}{\underset{\|}{C}}-$ |

TABLE VI-continued

[Structure: cyclohexane ring with CBz-N(CH₃)- at top left, B at top, =O, connected via O to a second ring with H, OR₁₀, O, and vinyl CH₂ group; B₁ at bottom left, H₃C-N-CBz at bottom]

| B | B₁ | R₁₀ |
|---|---|---|
| HO— | C₂H₅S— | CH₃CH₂C(=O)— |
| HO— | HO— | CH₃CH₂C(=O)— |
| HO— | HO— | CH₃(CH₂)₂C(=O)— |
| HO— | HO— | CH₃(CH₂)₂C(=O)— |
| HO— | HO— | CH₃(CH₂)₃C(=O)— |
| HO— | HO— | CH₃(CH₂)₃—C(=O)— |
| HO— | HO— | isopropionyl |
| HO— | HO— | sec-butyryl |
| HO— | HO— | t-butyryl |

PREPARATION 4a

N,N'-dicarbobenzyloxy-6'-methylspectinomycin

The N,N'-dicarbobenzyloxy-2-O'-6'-methylene-4',5'-didehydrospectinomycin (1.28 g, 1.93 mmole) is dissolved in 2-propanol (56.0 ml) and triethylamine (0.80 ml) and platinum oxide 0.96 g is added. Two such duplicate reactions are run. The mixture is allowed to shake at 20 psi of hydrogen for 3 hours. The catalyst is filtered on celite and the filtrate from the 2 reactions are combined; water (5 ml) is added and the mixture stirred at room temperature for 19 hours to remove the 2-O'-acetyl group. The solution is concentrated, the residue taken up in ½% methanol in chloroform (8 ml) and placed on an HPLC silica gel (140 g) column which has been wet packed in the same solvent. The mixture is eluted with ½% methanol in chloroform (3 liters), 1% (1 @2 liters), then 1¼% (4 liters).

Fractions are monitered by TLC (5% MeOH in CHCl₃) and pure fractions combined. The first product to be eluted is N,N'-dicarbobenzyloxy-6'-methylspectinomycin (0.97 g, 40% yield).

CD (CH₃OH): $[\theta]_{300}$ nm—1,150±1,100.

PMR (CDCl₃): 0.99 (3H, t), 2.97 (3H, s), 3.03 (3H, s), 4.64 (1H, s). 5.09 (4H, s), 7.27 ppm (10H, s).

CMR (CD₃COCD₃): 202.0, 157.5, 137.9, 129.0, 128.2, 97.4, 92.2, 74.9, 74.4, 72.8, 67.2, 66.3, 65.6, 60.4, 57.2, 43.7, 31.4, 28.8, 9.6 ppm.

Mass spectrum (diTMS): 830(M+), 815, 745, 629, 539, 493, 449, 380, 354, 342, 305, 181, 170, 14, 91, 73.

PREPARATION 4b

N,N'-dicarbobenzyloxy-6'-methylspectinomycin

The N,N'-dicarbobenzyloxy-2-O'-6'-methylene-4',5'-didehydrospectinomycin (1.28 g, 1.93 mmole) is dissolved in 2-propanol (56.0 ml) and triethylamine (0.80 ml) and platinum oxide 0.96 g is added. Two such duplicate reactions are run. The mixture is allowed to shake at 20 psi of hydrogen for 3 hours. The catalyst is filtered on celite and the filtrate from the 2 reactions are combined; water (5 ml) is added and the mixture stirred at room temperature for 19 hours to remove the 2-O'-acetyl group. The solution is concentrated, the residue taken up in ½% methanol in chloroform (8 ml) and placed on an HPLC silica gel (140 g) column which has been wet packed in the same solvent. The mixture is eluted with ½% methanol in chloroform (3 liters), 1% (1 @2 liters), then 1¼% (4 liters).

Fractions are monitered by TLC (5% MeOH in CHCl₃) and pure fractions combined. The first product to be eluted is N,N'-dicarbobenzyloxy-6'-methylspectinomycin (0.97 g, 40% yield).

CD (CH₃OH): $[\theta]_{300}$ nm—1,150±1,100.

PMR (CDCl₃): 0.99 (3H, t), 2.97 (3H, s), 3.03 (3H, s), 4.64 (1H, s). 5.09 (4H, s), 7.27 ppm (10H, s).

CMR (CD₃COCD₃): 202.0, 157.5, 137.9, 129.0, 128.2, 97.4, 92.2, 74.9, 74.4, 72.8, 67.2, 66.3, 65.6, 60.4, 57.2, 43.7, 31.4, 28.8, 9.6 ppm.

Mass spectrum (diTMS): 830(M+), 815, 745, 629, 539, 493, 449, 380, 354, 342, 305, 181, 170, 14, 91, 73.

PREPARATION 5

N,N'-dicarbobenzyloxy-6'-methylspectinomycin

To 3'-acetoxy-3'-methoxy-6'-methylspectinomycin (200 mg, 0.28 mmole) in tetrahydrofuran (20 ml) is added 0.1 hydrochloric acid (2.0 ml). The solution is allowed to stand at room temperature for 23 hours and then heated at 50° C. for 2½ hours. By this time TLC (5/95 methanol in chloroform) shows complete and clean conversion to N,N'-dicarbobenzyloxy-6'-methylspectinomycin. The solution is concentrated (to ~5 ml) and diluted with ethyl acetate. The organic phase is washed with brine (20+10 ml). Aqueous phases are then washed in sequence with ethyl acetate (20 ml). Organic extracts are dried over sodium sulfate and concentrated to yield 180 mg of N,N'-dicarbobenzyloxy-6'-methylspectinomycin (0.20 mmole, quantitative yield). The CMR is identical with that of a reference standard.

PMR (CDCl₃): 0.94 (3H, t), 1.88, 1.91 (3H, singlets), 2.92 (3H, s), 3.04 (3H, s), 3.79 (3H, s), 2.78 (1H, s), 5.08 (4H, s), 7.78 ppm (10H, s).

CMR (CD₃COCD₃): 172.9, 172.7, 157.6, 157.1, 138.1, 129.1, 128.4, 107.3, 96.6, 92.2, 75.1, 74.7, 71.0, 67.3, 66.3, 69.2, 6.1, 60.4, 60.3, 57.7, 57.1, 50.1, 35.0, 31.5, 28.1, 21.4, 21.3, 9.8 ppm.

Utilizing procedures similar to those used in Preparations 4a, 4b and 5, but substituting the appropriately substituted dienones for N,N'-dicarbobenzyloxy-2'O'-6'-methylene-4',5'-didehydrospectinomycin, there is obtained the protected spectinomycin analogs of Tables VII and VIII. In addition, the corresponding 3'-acyloxy-3'-alkoxy analogs that are obtained when the substitutions are made in preparation 4b, are shown in Tables IX and X.

TABLE VII

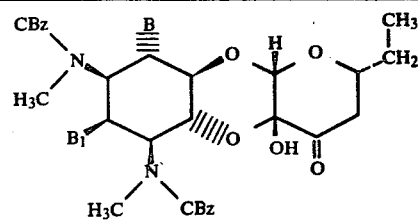

| B | B₁ |
|---|---|
| HO— | HO— |
| CH₃O— | HO— |
| C₂H₅O— | HO— |
| HS— | HO— |
| CH₃S— | HO— |
| C₂H₅S— | HO— |
| H— | HO— |
| HO— | H— |
| HO— | CH₃O— |
| HO— | C₂H₅O— |
| HO— | HS— |
| HO— | CH₃S— |
| HO— | C₂H₅S— |
| HO— | HO— |
| HO— | HO— |
| HO— | HO— |
| HO— | HO— |
| HO— | HO— |
| HO— | HO— |
| HO— | HO— |

TABLE VIII

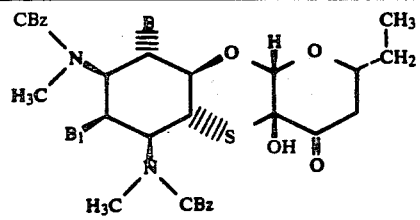

| B | B₁ |
|---|---|
| HO— | HO— |
| CH₃O— | HO— |
| C₂H₅O— | HO— |
| HS— | HO— |
| CH₃S— | HO— |
| C₂H₅S— | HO— |
| H— | HO— |
| HO— | H— |
| HO— | CH₃O— |
| HO— | C₂H₅— |
| HO— | H₂— |
| HO— | CH₃S— |
| HO— | C₂H₅S— |
| HO— | HO— |
| HO— | HO— |
| HO— | HO— |
| HO— | HO— |
| HO— | HO— |
| HO— | HO— |
| HO— | HO— |

TABLE IX

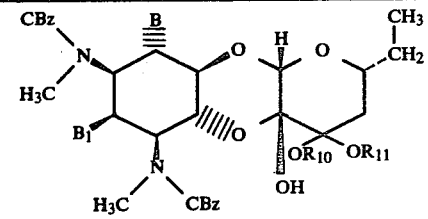

| B | B₁ | R₁₀ | R₁₁ |
|---|---|---|---|
| HO— | HO— | $CH_3\overset{O}{\underset{\|}{C}}$— | CH₃— |
| CH₃O— | HO— | $CH_3\overset{O}{\underset{\|}{C}}$— | CH₃— |
| C₂H₅O— | HO— | $CH_3\overset{O}{\underset{\|}{C}}$— | CH₃— |
| HS— | HO— | $CH_3\overset{O}{\underset{\|}{C}}$— | CH₃— |
| CH₃S— | HO— | $CH_3\overset{O}{\underset{\|}{C}}$— | CH₃— |
| C₂H₅S— | HO— | $CH_3\overset{O}{\underset{\|}{C}}$— | CH₃— |
| H— | HO— | $CH_3\overset{O}{\underset{\|}{C}}$— | CH₃— |
| HO— | H— | $CH_3\overset{O}{\underset{\|}{C}}$— | CH₃— |
| HO— | CH₃O— | $CH_3\overset{O}{\underset{\|}{C}}$— | CH₃— |
| HO— | C₂H₅O— | $CH_3\overset{O}{\underset{\|}{C}}$— | CH₃— |
| HO— | H₂ | $CH_3\overset{O}{\underset{\|}{C}}$— | CH₃— |
| HO— | CH₃S— | $CH_3\overset{O}{\underset{\|}{C}}$— | CH₃— |
| HO— | C₂H₅S— | $CH_3\overset{O}{\underset{\|}{C}}$— | CH₃— |
| HO— | HO— | $CH_3\overset{O}{\underset{\|}{C}}$— | C₂H₅— |
| HO— | HO— | $CH_3\overset{O}{\underset{\|}{C}}$— | C₃H₇— |
| HO— | HO— | $CH_3\overset{O}{\underset{\|}{C}}$— | C₄H₉— |
| HO— | HO— | $CH_3\overset{O}{\underset{\|}{C}}$— | C₅H₁₁— |
| HO— | HO— | $CH_3\overset{O}{\underset{\|}{C}}$— | C₆H₁₃— |

TABLE IX-continued

Structure: cyclohexane ring with CBz-N(CH3)-, B, =O, B1, N(CH3)(CBz), with side chain containing B, O, H, OR10, OR11, OH, O, CH2, CH3

| B | B | R10 | R11 |
|---|---|---|---|
| HO— | HO— | CH3C(=O)— | C7H15— |
| HO— | HO— | CH3C(=O)— | C8H17— |

TABLE X

Structure: similar cyclohexane with S substituent

| B | B1 | R10 | R11 |
|---|---|---|---|
| HO— | HO— | CH3C(=O)— | CH3— |
| CH3O— | HO— | CH3C(=O)— | CH3— |
| C2H5O— | HO— | CH3C(=O)— | CH3— |
| HS— | HO— | CH3C(=O)— | CH3— |
| CH3S— | HO— | CH3C(=O)— | CH3— |
| C2H5S— | HO— | CH3C(=O)— | CH3— |
| H— | HO— | CH3C(=O)— | CH3— |
| HO— | H— | CH3C(=O)— | CH3— |
| HO— | CH3O— | CH3C(=O)— | CH3— |
| HO— | C2H5— | CH3C(=O)— | CH3— |
| HO— | H2 | CH3C(=O)— | CH3— |

TABLE X-continued

| B | B1 | R10 | R11 |
|---|---|---|---|
| HO— | CH3S— | CH3C(=O)— | CH3— |
| HO— | C2H5S— | CH3C(=O)— | CH3— |
| HO— | HO— | C2H5C(=O)— | C2H5— |
| HO— | HO— | C3H7C(=O)— | C3H7— |
| HO— | HO— | C4H9C(=O)— | C4H9— |
| HO— | HO— | C5H11C(=O)— | C5H11— |
| HO— | HO— | C6H13C(=O)— | C6H13— |
| HO— | HO— | C7H15C(=O)— | C7H15— |
| HO— | HO— | C8H17C(=O)— | C8H17— |

EXAMPLE 1

6′-Methylspectinomycin and dihydrochloride hydrate thereof

N,N′-dicarbobenzyloxy-6′-methylspectinomycin (0.41 g, 0.66 mmole) is dissolved in absolute methanol (32 ml). Formic acid (1.61 ml) and palladium black (328 mg) are added and the mixture is stirred at room temperature for 1¾ hours. The solid is filtered and the filtrate concentrated finally at high vacuum. The residue, 6′-methylspectinomycin, is diluted with water (40 ml) and 1.0 N hydrochloric acid (1.5 ml) added. The solution is freeze dried to give solid salt (250 mg, 0.55 mmole as dihydrochloride hydrate, 84% yield).

CMR ($D_2O$; $CH_3CN$ as IS=O): 92.7, 91.0, 72.1, 68.8, 65.0, 64.6, 60.6, 58.6, 57.6, 38.0, 29.8, 29.3, 25.9, 7.6 ppm.

Mass spectrum (tetra TMS): 634($M^+$), 619, 532, 513, 442, 386, 287, 217, 188, 171, 145, 73.

Utilizing a procedure similar to that used in Example 1 but substituting the appropriately substituted protected 6′-methylspectinomycin for N,N′-dicarbobenzyloxy-6′-methylspectinomycin, there is obtained the 6′-methylspectinomycin analogs of Tables XI and XII.

TABLE XI
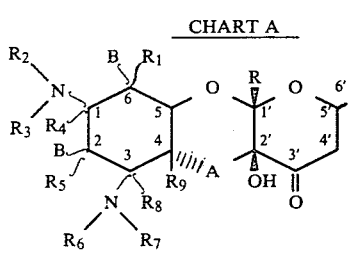
| B | $B_1$ |
|---|---|
| HO— | HO— |
| $CH_3O$— | HO— |
| $C_2H_5O$— | HO— |
| HS— | HO— |
| $CH_3S$— | HO— |
| $C_2H_5S$— | HO— |
| H— | HO— |
| HO— | H— |
| HO— | $CH_3O$— |
| HO— | $C_2H_5O$— |
| HO— | $H_2$— |
| HO— | $CH_3S$— |
| HO— | $C_2H_5S$— |
TABLE XII
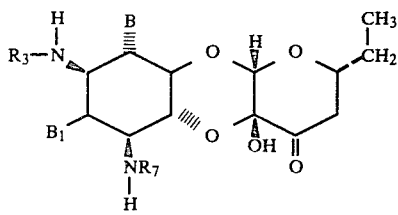
| B | $B_1$ |
|---|---|
| HO— | HO— |
| $CH_3O$— | HO— |
| $C_2H_5O$— | HO— |
| HS— | HO— |
| $CH_3S$— | HO— |
| $C_2H_5S$— | HO— |
| H— | HO— |
| HO— | H— |
| HO— | $CH_3O$— |
| HO— | $C_2H_5O$— |
| HO— | HS— |
| HO— | $CH_3S$— |
| HO— | $C_2H_5S$— |
CHART A
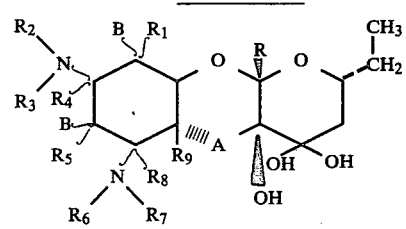  I
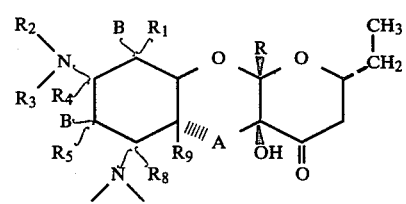  Ia
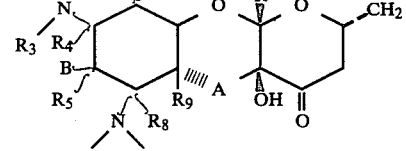  I'
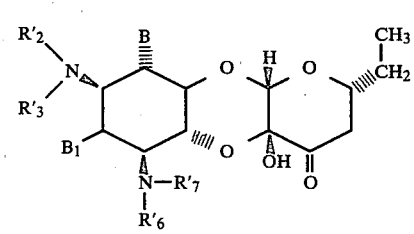  II
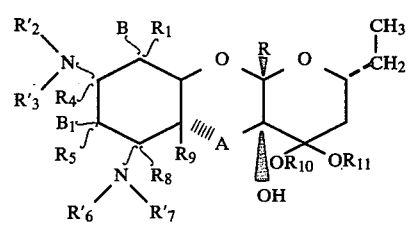  IIa
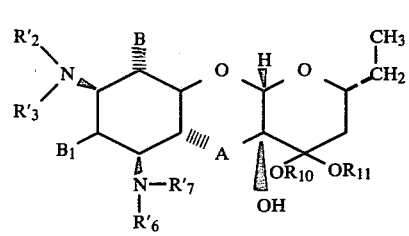  II'
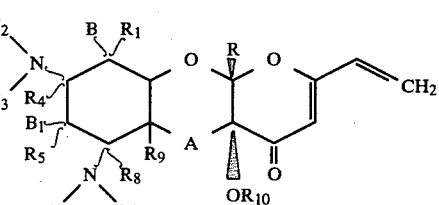  II'a
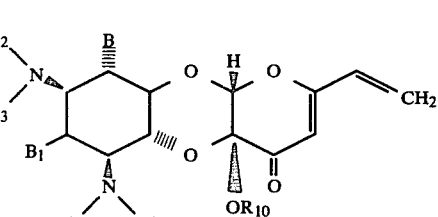  III
  IIIa 4,380,652
-continued
CHART A
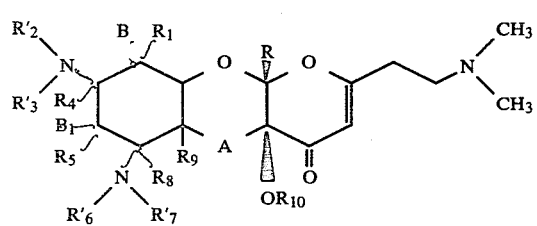
IV
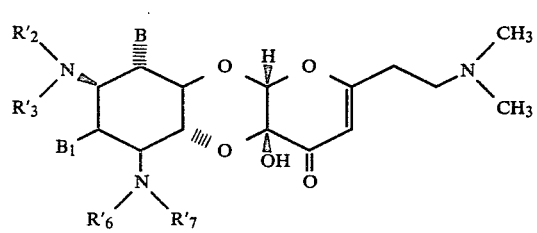
IVa
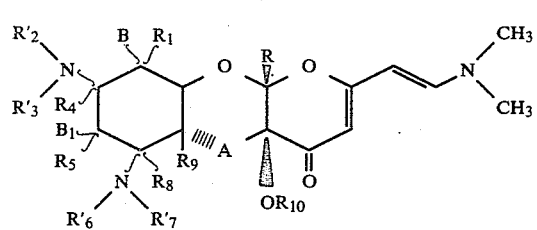
V
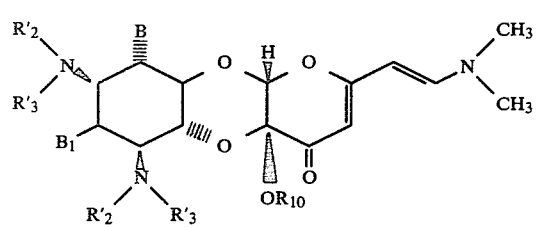
Va
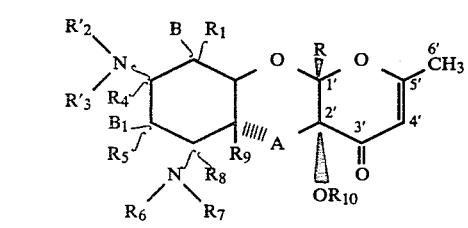
VI
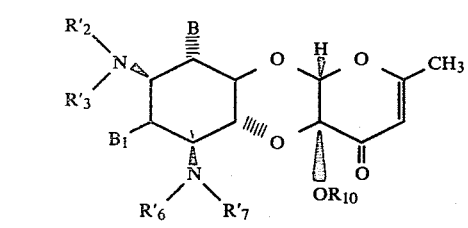
VIa
SCHEME 1
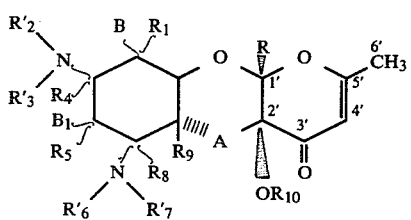
VI
STEP 1 | DMF, NMe₂, H–C(OCH₃)₂
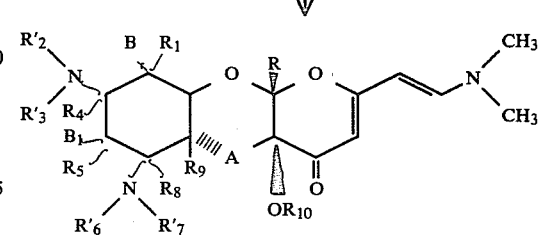
V
STEP 2 | pH 4, NaCNBH₄
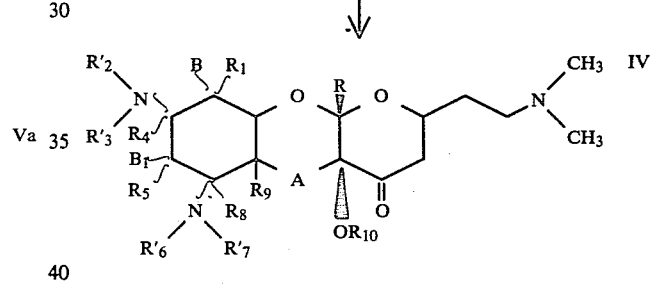
IV
STEP 3 | CH₃I
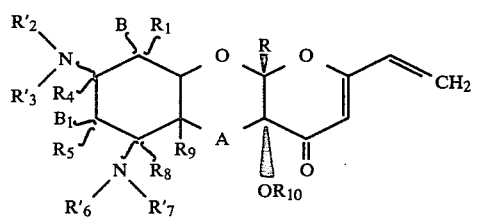
III
STEP 4 | Reduction, NEt₃
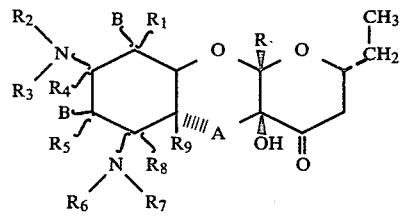
II
STEP 5 | Deprotection -continued
SCHEME 1

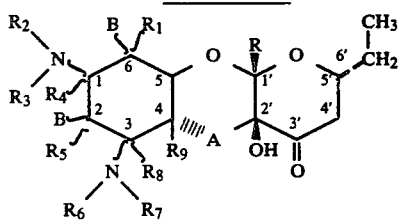

I claim:
1. A compound having the formula

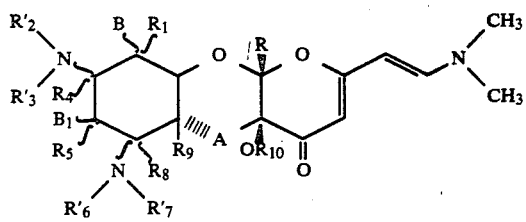

wherein R is hydrogen or alkyl and $R_1$, $R_4$, $R_5$, $R_8$, and $R_9$ are selected from the group consisting of hydrogen, lower alkyl, lower alkenyl, and lower alkylyl; B and $B_1$ are the same or different and are selected from the group consisting of hydrogen, hydroxy, alkoxy, o-lower alkenyl, thio, thio-lower alkyl and thio-lower alkenyl; A is selected from the group consisting of oxygen and sulfur; $R'_2$, $R'_3$, $R'_6$ and $R'_7$ are selected from the group consisting of lower alkyl, lower alkenyl, lower alkynyl, and a blocking group selected from the group consisting of aralkoxycarbonyl, halogenated-alkoxycarbonyl and alkoxycarbonyl; with the proviso that one of $R'_2$ and $R'_3$ is always a blocking group, and that one of $R'_6$ and $R'_7$ is always a blocking group; and $R_{10}$ is acyl.

2. A compound according to claim 1 having the formula

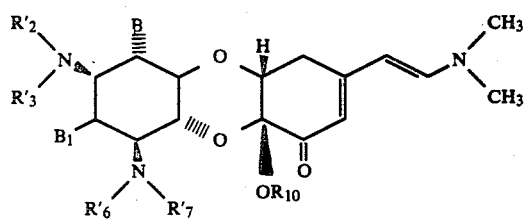

wherein $R'_2$, $R'_3$, $R'_6$, $R'_7$, $R_{10}$, B and $B_1$ are the same as in claim 1.

3. A compound according to claim 2, where $R'_2$ and $R'_6$ are hydrogen, $R'_3$ and $R'_7$ are carbobenzyloxy, $R_{10}$ is acetyl, B and $B_1$ are hydroxy, so that the specific embodiment is the enamine of N,N'-dicarbobenzyloxy-2'-O-acetyl-4',5'-didehydrospectinomycin.

4. A process for preparing a compound having the formula

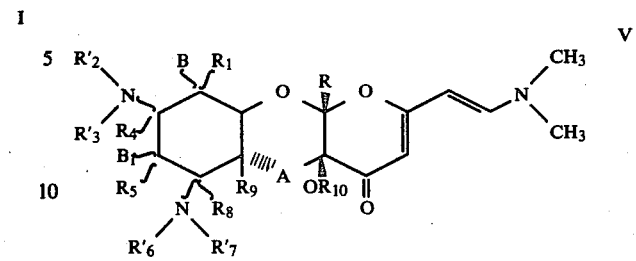

which comprises reacting a compound having the formula

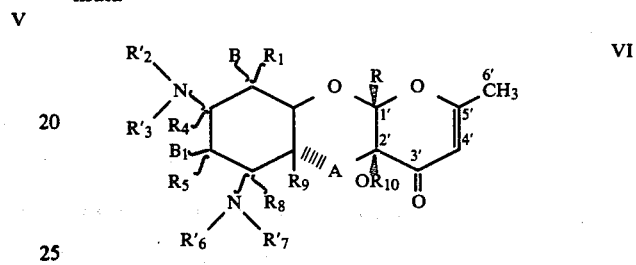

with, in an excess of an acetal of dimethylformamide wherein R is hydrogen or alkyl and $R_1$, $R_4$, $R_5$, $R_8$, and $R_9$ are selected from the group consisting of hydrogen, lower alkyl, lower alkenyl, and lower alkynyl; B and $B_1$ are the same or different and are selected from the group consisting of hydrogen, hydroxy, alkoxy, o-lower alkenyl, thio, thio lower alkyl and thio-lower alkenyl; A is selected from the group consisting of oxygen and sulfur; $R'_2$, $R'_3$, $R'_6$ and $R'_7$ are selected from the group consisting of lower alkyl, lower alkenyl, lower alkynyl, and a blocking group selected from the group consisting of aralkoxycarbonyl, halogenated-alkoxycarbonyl and alkoxycarbonyl; with the proviso that one of $R'_2$ and $R'_3$ is always a blocking group, and that one of $R'_6$ and $R'_7$ is always a blocking group; and $R_{10}$ is acyl.

5. A process according to claim 4 wherein the compound prepared has the formula

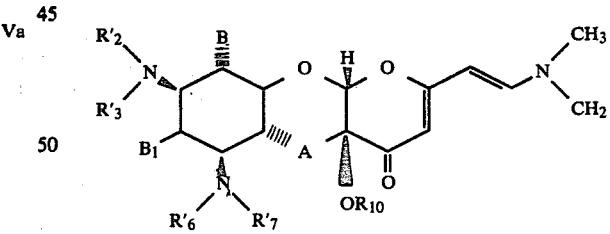

wherein $R'_2$, $R'_3$, $R'_6$, and $R'_7$ are selected from the group consisting of lower alkyl and a blocking group and B and $B_1$ are selected from the group consisting of hydrogen or lower alkoxy; and $R_{10}$ is acyl.

6. A process according to claim 5 wherein the compound prepared is the enamine of N,N'-dicarbobenzyloxy-2'-O-acetyl-4',5'-didehydrospectinomycin.

* * * * *